United States Patent [19]

Forbes et al.

[11] Patent Number: 6,025,367
[45] Date of Patent: Feb. 15, 2000

[54] SULFONAMIDE DERIVATIVES AS 5HT$_7$ RECEPTOR ANTAGONISTS

[75] Inventors: Ian Thomson Forbes, Stevenage; Shirley Katherine Rahman, Bishop's Stortford, both of United Kingdom

[73] Assignee: SmithKline Beecham plc, Brentford, United Kingdom

[21] Appl. No.: 09/202,781

[22] PCT Filed: Jun. 17, 1997

[86] PCT No.: PCT/EP97/03160

§ 371 Date: Jun. 23, 1999

§ 102(e) Date: Jun. 23, 1999

[87] PCT Pub. No.: WO97/49695

PCT Pub. Date: Dec. 31, 1997

[30] Foreign Application Priority Data

Jun. 25, 1996 [GB] United Kingdom .................... 9613261
Jun. 25, 1996 [GB] United Kingdom .................... 9613262

[51] Int. Cl.$^7$ ..................................................... A01N 43/42
[52] U.S. Cl. .......................... 514/307; 546/143; 546/146; 546/148
[58] Field of Search ............................ 514/307; 546/143, 546/146, 148

[56] References Cited

U.S. PATENT DOCUMENTS 4,485,108  11/1984  Jozic ........................................ 514/331
5,294,621  3/1994  Russell ..................................... 514/301

FOREIGN PATENT DOCUMENTS 0 064 445  11/1982  European Pat. Off. .
0 076 072   4/1983  European Pat. Off. .
0 306 375   3/1989  European Pat. Off. .
1580180     3/1968  France .

OTHER PUBLICATIONS

Kitagawa et al., Biochim. Biophys. Acta, 987 (1989) 235–8.

*Primary Examiner*—Fiona T. Powers
*Attorney, Agent, or Firm*—Soma G. Simon; William T. King; Charles M. Kinzig

[57] ABSTRACT

The invention relates to sulphonamide compounds of formula (I) or a salt thereof having pharmacological activity, processes for their preparation, to compositions containing them and to their use in the treatment of CNS disorders, wherein: Ar is an optionally substituted mono- or bicyclic aromatic or heteroaromatic ring; Ar' is an optionally substituted mono- or bicyclic aromatic or heteroaromatic ring; $R^1$ is $C_{1-6}$alkyl or together with the group $R^3$ form a 5–8 membered ring containing one or two heteroatoms optionally substituted by $C_{1-6}$alkyl; $R^2$ is hydrogen or $C_{1-6}$alkyl; $R^3$ is hydrogen, $C_{1-6}$alkyl or together with the group $R^1$ form a 5–8 membered ring containing one or two heteroatoms optionally substituted by $C_{1-6}$alkyl; $R^4$ is hydrogen or $C_{1-6}$alkyl; $R^5$ and $R^6$ are independently hydrogen or $C_{1-6}$alkyl; p is 1, 2 or 3; q is 1 to 3; and r is 1 or 2.

7 Claims, No Drawings

SULFONAMIDE DERIVATIVES AS 5HT$_7$ RECEPTOR ANTAGONISTS

This invention relates to compounds having pharmacological activity, processes for their preparation, to compositions containing them and to their use in the treatment of CNS disorders.

EPA 0 021 580 and EPA 0 076 072 describe sulphonamide derivatives which are disclosed as having antiarrhythmic activity. A structurally distinct class of compounds has now been discovered, which have been found to have 5HT$_7$ receptor antagonist activity. 5HT$_7$ receptor antagonists are believed to be of potential use in the treatment of certain CNS disorders such as anxiety, depression, sleep disorders, and schizophrenia.

The present invention therefore provides, in a first aspect, a compound of formula (I) or a salt thereof:

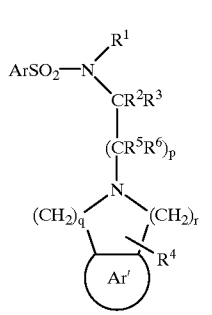

(I)

wherein:
- Ar is an optionally substituted mono- or bicyclic aromatic or heteroaromatic ring;
- Ar' is an optionally substituted mono- or bicyclic aromatic or heteroaromatic ring;
- $R^1$ is $C_{1-6}$alkyl or together with the group $R^3$ form a 5–8 membered ring containing one or two heteroatoms optionally substituted by $C_{1-6}$alkyl;
- $R^2$ is hydrogen or $C_{1-6}$alkyl;
- $R^3$ is hydrogen, $C_{1-6}$alkyl or together with the group $R^1$ form a 5–8 membered ring containing one or two heteroatoms optionally substituted by $C_{1-6}$alkyl;
- $R^4$ is hydrogen or $C_{1-6}$alkyl;
- $R^5$ and $R^6$ are independently hydrogen or $C_{1-6}$alkyl;
- p is 1, 2 or 3;
- q is 1, 2 or 3; and
- r is 1 or 2.

$C_{1-6}$alkyl groups, whether alone or as part of another group, may be straight chain or branched.

Optional substituents for aromatic and heteroaromatic groups include $C_{1-6}$alkyl optionally substituted by $NR^7R^8$, $C_{2-6}$alkenyl, $C_{2-6}$alkynyl, $C_{1-6}$alkylthio, cyano, nitro, halogen, $CF_3$, $C_2F_5$, $NR^7R^8$, $CONR^7R^8$, $NR^7COR^8$, $S(O)_p$ $NR^7R^8$, CHO, $OCF_3$, $SCF_3$, $SOR^9$, $SO_2R^9$, $OSO_2R^9$, $COR^9$, $CH_2OR^9$, $CO_2R^9$ or $OR^9$ where p is 1 or 2 and $R^7$, $R^8$ and $R^9$ are independently hydrogen, $C_{1-6}$alkyl, optionally substituted aryl or optionally substituted aryl$C_{1-6}$alkyl. More than one substituent can be present and in the case of multiple substituents these can be the same or different.

Preferably Ar is an optionally substituted bicyclic aromatic group. Most preferably Ar is naphthyl.

Preferably Ar' is an optionally substituted monocyclic aromatic group. Most preferably Ar' is phenyl.

Examples of groups where $R^1$ is $C_{1-6}$alkyl are ethyl and most preferably methyl. When groups $R^1$ and $R^3$ are combined to form a heterocycle the preferred examples have 5 or most preferably 6 membered rings.

Preferably $R^2$ is hydrogen or methyl;

The preferred group when $R^3$ is $C_{1-6}$alkyl is methyl. When groups $R^1$ and $R^3$ are combined to form a heterocycle the preferred examples have 5 or most preferably 6 membered rings.

Preferably $R^4$ is hydrogen;

Preferably $R^5$ and $R^6$ are hydrogen;

Preferably q and r have values such that they form part of a 5- or 6-membered ring. Most preferably q and r have values such that they form part of a 6-membered ring i.e. the sum of q and r is 3.

Particular compounds of the invention include:
2-(2-[1-Naphthalene-1-sulfonyl)piperidin-2-yl]-ethyl)-1,2,3,4-tetrahydroisoquinoline 2-(2-(3-Chloro-4-methylphenyl)-piperidin-2-yl)-ethyl-1,2,3,4 tetrahydroisoquinoline and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulfonic.

Compounds of formula (I) may also form solvates such as hydrates, and the invention also extends to these forms. When referred to herein, it is understood that the term 'compound of formula (I)' also includes these forms.

Certain compounds of formula (I) are capable of existing in stereoisomeric forms including diastereomers and enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises (a) the coupling of a compound of formula (II):

(II)

in which Ar is as defined in formula (I) and L is a leaving group with a compound of formula (III):

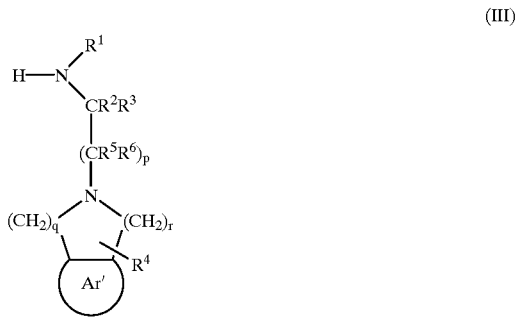

(III)

in which p, q, r, $R^2$, $R^3$, $R^4$, $R^5$, $R^6$ and Ar' are as defined in formula (I); or (b) the coupling of a compound of formula (IV):

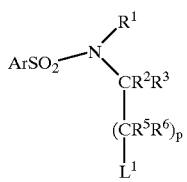

(IV)

in which Ar, p, $R^1$, $R^2$, $R^3$, $R^5$ and $R^6$ are as defined in formula (I) and $L^1$ is a leaving group with a compound of formula (V):

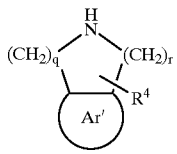

(V)

in which q, r, $R^4$ and Ar' are as defined in formula (I) and optionally thereafter (a) or (b):

forming a pharmaceutically acceptable salt.

Suitable leaving groups L and $L^1$ include halogen, in particular chloro. The reaction of a compounds of formulae (II) and (III) is preferably carried out in an inert solvent such as dichloromethane optionally in the presence of a base such as triethylamine.

Compounds of formulae (II), (III), (IV) and (V) are either commercially available or may be prepared according to known methods or analogous to known methods. Novel compounds of formulae (II), (III), (IV) and (V) form a further aspect of the invention.

Pharmaceutically acceptable salts may be prepared conventionally by reaction with the appropriate acid or acid derivative.

Compounds of formula (I) and their pharmaceutically acceptable salts have $5HT_7$ receptor antagonist activity and are believed to be of potential use for the treatment or prophylaxis of CNS disorders such as anxiety, depression, sleep disorders, including instances of Circadian rhythym and schizophrenia.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising, a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

DESCRIPTION 1

2-(2-Chloroethyl)-1-(naphthalene-1-sulfonyl) piperidine (D1)

To a solution of 1-naphthalene sulfonyl chloride (26.64 g) in toluene (300 ml) was added 2-piperidine ethanol (8.99 g) and diisopropylethylamine (26.8 ml). The mixture was heated to reflux overnight. After cooling to room temperature the solvent was concentrated in vacuo and the residue chromatographed on silica eluting with 50% ethyl acetate and petroleum ether (bp 60–80). The title compound was isolated as an oil, which solidified on standing (12.5 g, 53%). $MH^+338$.

2-[1-(naphthalene-1-sulfonyl)-piperidin-2-yl]ethanol the more polar product was isolated as an oil (9.8 g, 44%).

DESCRIPTION 2

2-(2-Hydroxyethyl)-piperidine-1-carboxylic acid benzyl ester (D2)

2-Piperidine ethanol (39.6 ml, 0.31 mol) was dissolved in 5M aq NaOH (62 ml, 0.31 mol) and dioxan (100 ml). The mixture was cooled to 0° C. and treated with benzyl chloroformate (45.3 ml, 0.32 mol) and 5M NaOH (62 ml, 0.31 mol). Stirring was continued at room temp. for 18 hours.ABioxan was removed in vacuo and the aqueous phase extracted with ether before acidifying with 5N HCl and extracting again with ether. The organic phase was dried and evaporated in vacuo and the residue purified by chromatography on silica gel to give the title compound (77.2 g. 95%). MH$^+$264.

DESCRIPTION 3

2-[2-(3,4-Dihydro-1H-isoquinolin-2-yl)ethyl] piperidine-1-carboxylic acid benzyl ester (D3)

To a solution of 2-(2-hydroxyethyl)-piperidine-1-carboxylic acid benzyl ester (D2, 20 g, 76 mmol) in dichloromethane (400 ml) was added triethylamine (21 ml, 152 mmol) and methanesulfonic anhydride (20 g, 114 mmol) at 0° C. Stirring was continued for 1 hr. The reaction mixture was washed with sat. aq. NaHCO$_3$, dried and concentrated to afford the crude mesylate. This was dissolved in dichloromethane (150 ml) and treated with 1,2,3,4-tetrahydroisoquinoline (21 ml, 167 mmol). Stirring was continued for 48 hrs. The reaction mixture was partitioned between H$_2$O and CH$_2$Cl$_2$. The organic phase was dried and concentrated and the residue purified by chromatography on silica gel to afford the title compound (13 g, 49%). MH$^+$379.

DESCRIPTION 4

2-(2-Piperidin-2-yl ethyl)-1,2,3,4-tetrahydroisoquinoline (D4)

The protected amine 2-[2-(3,4-dihydro-1H-isoquinolin-2-yl)ethyl]piperidine-1-carboxylic acid benzyl ester (D3, 14 g, 0.037 mol) was dissolved in ethanol (300 ml) and hydrogenated over 10% Pd/C for 18 hours to afford the title compound (9 g, 100%). MH$^+$245.

EXAMPLE 1

2-(2-[1-Naphthalene-1-sulfonyl)piperidin-2-yl]-ethyl)-1,2,3,4-tetra hydroisoquinoline (E1)

To a solution of 2-(2-chloroethyl)-1-(naphthalene-1-sulfonyl)-piperidine (D1, 250 mg) in acetonitrile (20 ml) was added sodium iodide (12 mg), potassium carbonate (108 mg) and 1,2,3,4-tetrahydroisoquinoline (117 µl). The mixture was heated at reflux overnight. After cooling to room temperature the solvent was removed under reduced pressure. The residue was chromatographed on silica eluting with 5% methanol in dichloromethane to afford pure title compound as a foam (127 mg, 40%) MH$^+$435.

Examples E2–12 were Prepared using the Procedure Outlined in Example 1 using 2-(2-chloroethyl)-1-(naphthalene-1-sulfonyl)piperidine (D1) and an Appropriately Substituted 1,2,3,4 Tetrahydroisoquinoline

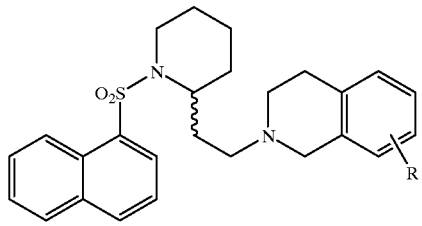

| Example | R | MH$^+$ |
|---|---|---|
| 2 | 7-Nitro | 480 |
| 3 | 7-Methylsulfonyl | 513 |
| 4 | 7-Sulphamoyl | 514 |
| 5 | 6-Methoxy | 465 |
| 6 | 7-Methoxy | 465 |
| 7 | 5-Acetylamino | 492 |
| 8 | 8-Chloro | 469/471 |
| 9 | 6,7-Dimethoxy | 495 |
| 10 | 7-Benzoyl | 539 |
| 11 | 7-Phenoxy | 527 |
| 12 | 8-Phenyl | 511 |

EXAMPLE 13

(±) 7-Amino-2-(2-[1-(naphthalene-1-sulfonyl) piperidin-2-yl]ethyl)-1,2,3,4-tetrahydroisoquinoline (E13)

A warm solution of 7-nitro-2-(2-[1-(naphthalene-1-sulfonyl) piperidin-2-yl]ethyl)-1,2,3,4-trahydroisoquinoline (E2) (22 mmol) in methanol (300 ml) was added to a solution of ammonium chloride (6.0 g) in water (100 ml) containing iron powder (3.8 g). The mixture was heated to reflux for 5 hours. The mixture was filtered whilst hot and the methanol was subsequently removed in vacuo. The crude product was crystallised from ethyl acetate/methanol to give the title compound (5.9 g, 58%) mpt 212–218° C. MH$^+$450.

EXAMPLE 14

(±) 7Bromo-2-(2-[1-(naphthalene-1-sulfonyl) piperidin-2-yl]ethyl)-1,2,3,4-tretahydroisoquinoline (E14)

To a solution of 7-amino-2-(2-[1-(naphthalene-1-sulfonyl) piperidin-2-yl]ethyl)-1,2,3,4-tetrahydroisoquinoline (E13) (4 g, 8.9 mmol) in 45% HBr at 0° C. was added sodium nitrite (0.65 g) in water (5 ml). The resulting mixture was added portionwise to a solution of copper (I) bromide (0.75 g) in hydrobromic acid (3 ml). When effervesence had ceased, the mixture was partitioned between 40% aqueous NaOH and CH$_2$Cl$_2$/MeOH. The organic phase was separated, filtered, dried and evaporated. The residue was purified on silica to afford the title compound (2.73 g, 60%). MH$^+$513/515.

Examples E15–24 were Prepared by the Following Generic Procedure

A mixture of (±) 7-bromo-2-(2-[1-naphthalene-1-sulfonyl) piperidin-2-yl]ethyl-1,2,3,4-tetrahydroisoquinoline (E14) (1 mmol), and an arylboronic acid (1 mmol), sodium carbonate (4 mmol), tetrakis(triphenylphosphine)palladium (0) (0.03 mmol) in 1,2 DME and water (1:1, 20 ml) was heated to reflux for 3 hrs. After removal of the DME, the product was extracted with CH$_2$Cl$_2$. The organic phase was washed with brine, dried and concentrated. The crude product was converted to its hydrochloride salt with 1M HCl in Et$_2$O.

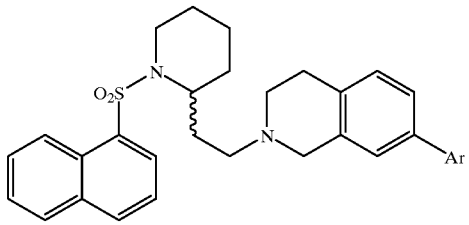

| Example | Ar | MH$^+$ |
|---|---|---|
| 15 | Phenyl | 511 |
| 16 | 2-Methylphenyl | 525 |
| 17 | 4-Methylphenyl | 525 |
| 18 | 4-Trifluoromethylphenyl | 579 |
| 19 | 3-Trifluoromethylphenyl | 579 |
| 20 | 3-Methoxyphenyl | 541 |
| 21 | 3-Pyridyl | 512 |
| 22 | 2-Methoxyphenyl | 541 |
| 23 | 4-Methoxyphenyl | 541 |
| 24 | 3-Chlorophenyl | 545/547 |

EXAMPLE 25

(±) 2-(2-[1-(Naphthalene-1-sulfonyl)piperidin-2-yl] ethyl)-1,2,3,4-tetrahydro-7-trifluoromethyl isoquinoline (E25)

A mixture of 7-bromo-2-(2-[1-naphthalene-1-sulfonyl) piperidin-2-yl]ethyl-1,2,3,4-tetrahydroisoquinoline (E14) (0.5 g, 0.97 mmol), potassium trifluoroacetate (3 mmol) and copper (I) iodide (0.56 g) in toluene (3 ml) and DMF (5 ml) was heated to 135° C., for 24 hrs. The mixture was filtered and evaporated and the residue partitioned between ethyl acetate and water. The organic phase was washed with brine, dried and concentrated in vacuo. Purification by chromatography on silica gave the title compound. MH$^+$503.

EXAMPLE 26

(±) 6-Hydroxy-2-(2-[1-(naphthalene-1-sulfonyl) piperidin-2-yl]ethyl)- 1,2,3,4-tetrahydroisoquinoline (E26)

Boron tribromide (1M in CH$_2$Cl$_2$) (6.6 ml) was added to a solution of 6-methoxy-2-(2-[1-(naphthalene-1-sulfonyl) piperidin-2-yl]ethyl-1,2,3,4-tetrahydroisoquinoline (E5) (0.5 g, 1.1 mmol) in dichloromethane (20 ml). The mixture was stirred at room temp. overnight and then poured onto ice cold conc. ammonia solution. The organic phase was washed with brine, dried and concentrated. Purification by chromatography on silica gel afforded the title compound (0.2 g, 40%). MH$^+$451.

EXAMPLE 27

(±) 6-Phenyl-2-(2-[1-(naphthalene-1-sulfonyl) piperidin-2-yl]ethyl)- 1,2,3,4-tetrahydroisoquinoline (E27)

To a solution of (±) 6-hydroxy-2-(2-[1-(naphthalene-1-sulfonyl)piperidin-2-yl]ethyl)-1,2,3,4-tetrahydroisoquinoline (E26) (0.16 g, 0.35 mmol) in pyridine (2 ml) at 0° C. was added trifluoromethane sulfonic anhydride (0.39 mmol). After stirring for 48 hrs the mixture was concentrated, dissolved in dichloromethane, washed with water, dried and concentrated to give the 6-trifluoromethane sulphonate derivative (0.18 g, 66%). This compound was converted to the title compound using phenylboronic acid and the method described in Example 15. MH$^+$511.

EXAMPLE 28

(±) 5-Amino-2-(2-[1-(naphthalene-1-sulfonyl) piperidin-2-yl]ethyl)- 1,2,3,4-tetrahydroisoquinoline (E28)

A mixture of the 5-acetylamino compound (Example 7) (1.1 g, 2.2 mmol) and 20% aqueous NaOH (3.5 ml) in EtOH (20 ml) was heated to reflux for 48 hrs. The mixture was concentrated and the residue dissolved in CH$_2$Cl$_2$. The solution was extracted twice with 5M HCl. The acidic extracts were basified with 40% NaOH and extracted with CH$_2$Cl$_2$. The organic extract was concentrated and the residue purified by chromatography on silica gel to afford the title compound (0.51 g, 51%). MH$^+$450.

EXAMPLE 29

(±) 5-Bromo-2-(2-[1-(naphthalene-1-sulfonyl) piperidin-2-yl]ethyl- 1,2,3,4-tetrahydroisoquinoline (E29)

The 5-amino compound (Example 28) (0.43 g, 0.96 mmol) was converted to the title compound using the method described in Example 14 (0.31 g, 63%). MH$^+$513/515.

EXAMPLE 30

(±) 2-(2-[1-(Naphthalene-1-sulfonyl)piperidine-2-yl] ethyl)-5-phenyl-1,2,3,4-tetrahydroisoquinoline (E30)

The title compound was prepared according to the procedure outlined in Example 15 using (±) 5-bromo-2-(2-[1-(naphthalene-1-sulfonyl)piperidin-2-yl]ethyl-1,2,3,4-tetrahydroisoquinoline (E29) and phenyl boronic acid. MH$^+$511.

EXAMPLE 31

(±) 7-Benzyloxy-2-(2-[1-(naphthalene-1-sulfonyl) piperidin-2-yl]ethyl)- 1,2,3,4-tetrahydroisoquinoline (E31)

The 7-methoxy compound (Example 6) (0.93 g, 2 mmol) was treated with BBr$_3$ as described in Example 26 to give the 7-hydroxy derivative (0.13 g, 15%). Alkylation of this compound with 80% sodium hydride 0.25 mmol and benzyl bromide (0.22 mmol) in THF afforded the title compound (40 mg, 34%). MH$^+$541.

Example 32–44 were Prepared by the Following Generic Procedure

To a stirred solution of 2-(2-piperidin-2-yl-ethyl)-1,2,3,4-tetrahydroisoquinoline (D4) (1 mmol) and diisopropylethylamine (1 mmol) in dichloromethane cooled by an ice bath was added an aryl sulfonyl chloride (1 mmol). Stirring was continued allowing the solution to reach room temperature over 24 hours. The solution was washed thoroughly (10% NaOH) and brine, dried and concentrated in vacuo. The residue was purified by chromatography on silica gel.

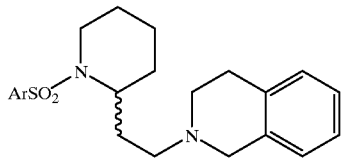

| Example | Ar | MH+ |
|---|---|---|
| 32 | 4,5-Dibromo-2-thiophene | 549 |
| 33 | 2-Bromophenyl | 463/465 |
| 34 | 3-Bromophenyl | 463/465 |
| 35 | 4-Bromophenyl | 463/465 |
| 36 | 2-Naphthyl | 435 |
| 37 | 4-Iodophenyl | 510 |
| 38 | 4-tert Butylphenyl | 441 |
| 39 | 4-n-Propylphenyl | 427 |
| 40 | 3-Methylphenyl | 399 |
| 41 | 4-Chloro-2,5-dimethylphenyl | 447 |
| 42 | 4-Cyanophenyl | 410 |
| 43 | 3-Chloro-4-methyl | 433 |
| 44 | 3,4-Dibromophenyl | 541/543/545 |

Example 45–52 were Prepared According to the Procedure Outlined in Example 32–44 using 7-phenyl-2-(2-piperidin-2-yl-ethyl)-1,2,3,4-tetrahydroisoquinoline and an aryl sulfonyl chloride

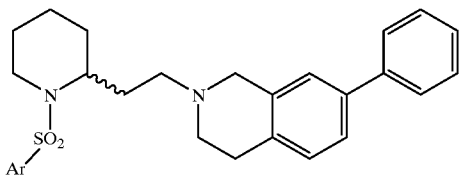

| Example | Ar | MH+ |
|---|---|---|
| 45 | 2-Naphthyl | 511 |
| 46 | 3,4-Dichlorophenyl | 529/531 |
| 47 | 4,5-Dibromo-2-thiophene | 623/625/627/629 |
| 48 | 4-Bromophenyl | 539/541 |
| 49 | 3-Chloro-4-methylphenyl | 509/511 |
| 50 | 4-Chloro-3,6-dimethylphenyl | 523/525 |
| 51 | 4-tert Butylphenyl | 517 |
| 52 | 3-Bromophenyl | 539/541 |

Pharmacological Data

[$^3$H]-5-Carboxamidotryptamine binding to human 5-HT$_7$ receptor clones expressed in 293 cells in vitro.

The affinity of test drugs for the 5-HT$_7$ receptor binding site can be determined by assessing their ability to displace [$^3$H]-5-carboxamidotryptamine from 5-HT$_7$ receptor clones expressed in 293 cells (To et al., 1995 and Sleight et al., 1995).

The cells suspension (400 μl) was incubated with [$^3$H]-5-carboxamido-tryptamine (0.5 nM) in Tris HCl buffer (pH 7.4) at 37° C. for 45 mins. Non-specific binding was measured in the presence of 5-hydroxytryptamine ($10^{-6}$M). Ten concentrations of test drug ($10^{-11}$ to $10^{-5}$M final concentration) were added in a volume of 50 ul. The total assay volume was 500 μl. Incubation was stopped by rapid filtration using a Tomtec cell harvester and radioactivity measured by scintillation counting on a Packard Topcount. The IC$_{50}$ values and pKi values were calculated by INFLEXION, a non-linear iterative curve fitting programme based in EXCEL (Bowen and Jerman, 1994).

Bowen, W. and Jerman, J. (1994). Br. J. Pharmacol., 112, 440P.

Sleight, A. J., Carolo, C., Petit, N., Zweingelstein, C. and Bourson, A. (1995). Mol. Pharmacol., 47, 99.

To, Z. P., Bonhaus, D. W., Eglen, R. M. and Jakeman, L. B. (1995). Br. J. Pharmacol., 15. 107.

All the compounds of examples 1 to 52 showed activity in the above test.

We claim:

1. A compound of formula (I) or a salt thereof:

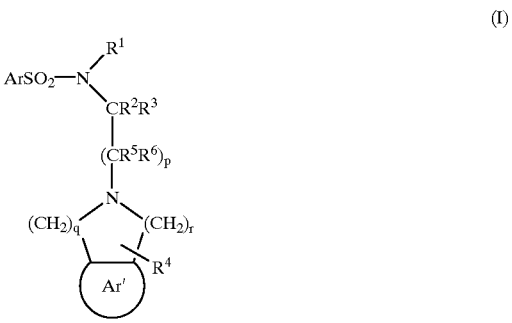

(I)

wherein:

Ar is an optionally substituted mono- or bicyclic aromatic or heteroaromatic ring;

Ar' is an optionally substituted mono- or bicyclic aromatic or heteroaromatic ring;

$R^1$ is $C_{1-6}$alkyl or together with the group $R^3$ form a 5–8 membered ring containing one or two heteroatoms optionally substituted by $C_{1-6}$alkyl;

$R^2$ is hydrogen or $C_{1-6}$alkyl;

$R^3$ is hydrogen, $C_{1-6}$alkyl or together with the group $R^1$ form a 5–8 membered ring containing one or two heteroatoms optionally substituted by $C_{1-6}$alkyl;

$R^4$ is hydrogen or $C_{1-6}$alkyl;

$R^5$ and $R^6$ are independently hydrogen or $C_{1-6}$alkyl;

p is 1, 2 or 3;

q is 1 to 3; and r is 1 or 2.

2. A compound according to claim 1 in which Ar is an optionally substituted bicyclic aromatic group.

3. A compound according to claim 1 in which Ar' is an optionally substituted monocyclic aromatic group.

4. A compound according to claim 1 which is:
2-(2-[1-Naphthalene-1-suffonyl)piperidin-2-yl]-ethyl)-1,2,3,4-tetra hydroisoquinoline
2-(2-(3-Chloro-4-methylphenyl)-piperidin-2-yl)-ethyl-1,2,3,4 tetrahydroisoquinoline and pharmaceutically acceptable salts thereof.

5. A pharmaceutical composition which comprises a compound according to claim 1 and a pharmaceutically acceptable carrier or excipient.

6. A process for the preparation of a compound of formula (I) as claimed in claim 1 or a pharmaceutically acceptable salt thereof, which process comprises:

(a) the coupling of a compound of formula (II):

ArSO$_2$L           (II)

in which Ar is as defined in claim 1 and L is a leaving group with a compound of formula (III):

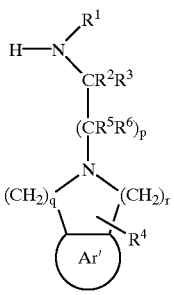

(III)

in which p, q, r, $R^2$, $R^3$, $R^4$, $R^5$, $R^6$ and Ar' are as defined in claim 1; or (b) the coupling of a compound of formula (IV):

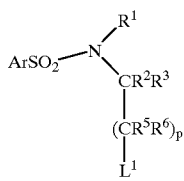

(IV)

in which Ar, $R^1$, $R^2$, $R^3$, $R^5$ and $R^6$ are as defined in claim 1 and $L^1$ is a leaving group with a compound of formula (V):

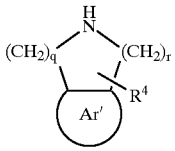

(V)

in which q, r, $R^4$ and Ar' are as defined in claim 1 and optionally thereafter (a) or (b):

forming a pharmaceutically acceptable salt.

7. A method of treating anxiety and/or depression comprising administering a compound according to claim 1.

* * * * *